United States Patent [19]

Colpan et al.

[11] Patent Number: 5,990,301
[45] Date of Patent: Nov. 23, 1999

[54] PROCESS FOR THE SEPARATION AND PURIFICATION OF NUCLEIC ACIDS FROM BIOLOGICAL SOURCES

[75] Inventors: Metin Colpan, Essen; Joachim Schorr, Düsseldorf; Peter Moritz, Kerpen, all of Germany

[73] Assignee: Qiagen GmbH, Hilden, Germany

[21] Appl. No.: 08/687,529

[22] PCT Filed: Feb. 3, 1995

[86] PCT No.: PCT/EP95/00389

§ 371 Date: Oct. 18, 1996

§ 102(e) Date: Oct. 18, 1996

[87] PCT Pub. No.: WO95/21177

PCT Pub. Date: Aug. 10, 1995

[30] Foreign Application Priority Data

Feb. 7, 1994 [DE] Germany .............................. 44 03 692
Jun. 25, 1994 [DE] Germany .............................. 44 22 291
Sep. 14, 1994 [DE] Germany .............................. 44 31 125

[51] Int. Cl.⁶ .............................. C07H 21/00; C12N 1/08
[52] U.S. Cl. .................... 536/25.4; 536/25.3; 536/25.31; 536/25.41; 536/25.42; 435/6; 435/259; 435/267; 435/270; 435/810
[58] Field of Search .............................. 536/25.3, 25.31, 536/25.4, 25.41, 25.42; 435/6, 259, 267, 268, 269, 270, 810

[56] References Cited

U.S. PATENT DOCUMENTS 4,997,932  3/1991  Reardon et al. .
5,057,426  10/1991  Henco et al. .......................... 435/270
5,652,141  7/1997  Henco et al. .......................... 435/270
5,747,663  5/1998  Colpan et al. ........................ 536/25.4

FOREIGN PATENT DOCUMENTS

90/05018  5/1990  WIPO .
93/11221  10/1993  WIPO .

OTHER PUBLICATIONS

Patent Abstract of Japan, Derwent Publications Ltd., JPA58013519 (Seikagaku Kogyo KK), Jan. 26, 1983.

*Primary Examiner*—James O. Wilson
*Attorney, Agent, or Firm*—Jacobson, Price, Holman & Stern, PLLC

[57] ABSTRACT

A process for the isolation and purification of nucleic acids and/or oligonucleotides for use in gene therapy wherein nucleic acids and/or oligonucleotides are isolated or purified from an essentially biological source, characterized in that essentially biological sources are lysed, the fractions obtained are optionally freed or depleted from the remainder of biological sources by per se known mechanical methods, such as centrifugation, filtration;

the fractions thus treated are subsequently treated with affinity chromatographic material or with inorganic chromatographic material for the removal of endotoxins; followed by isolation of nucleic acids and/or oligonucleotides on an anion exchanger which is designed such that DNA begins to desorb from the anion exchanger only at an ionic strength corresponding to a sodium chloride solution of a concentration higher by at least 100 mM than one corresponding to the ionic strength at which RNA begins to desorb from the anion exchanger material.

17 Claims, No Drawings

PROCESS FOR THE SEPARATION AND PURIFICATION OF NUCLEIC ACIDS FROM BIOLOGICAL SOURCES

The present invention pertains to a process for the isolation and purification of nucleic acids and/or oligonucleotides for use in gene therapy wherein said nucleic acids and/or oligonucleotides are purified from an essentially biological source, the use of anion exchange materials for the separation, purification and isolation of nucleic acids for the preparation of an agent containing nucleic acids for gene therapy, and a kit containing components for performing the process according to the invention.

A new form of therapy for genetically caused diseases, such as cystic fibrosis or muscular dystrophy, is based on the discovery that such diseases are caused by particular genetic defects. A therapy for the genetic defect appears to be possible if the healthy gene is supplied to the afflicted organism in a sufficient amount. Gene therapy not only enables the treatment of genetically caused diseases, but is also suitable for the treatment of tumors, and is suited as a new form of inoculation against infectious diseases, such as hepatitis, influenza, and HIV, to give but a few examples (TIBTECH, Special Issue: Gene Therapy Therapeutic Strategy and Commercial Prospects, May 1993, Vol. 11, No. 5 (112)).

A central problem of gene therapy is to administer the therapeutic DNA in such a manner that it will reach the scene of action. To date, part of the cells to be treated, in which the defect gene is expressed, such as blood cells, has been withdrawn from the patients. These cells have been cultured in culture dishs (in vitro). In order to introduce the therapeutically active foreign DNA into the cells, gene segments of a retrovirus, e.g., have been used which were linked to the DNA to be introduced. The genetically altered cells have been retransferred into the organism (Anderson, W. F. (1992), Human Gene Therapy, Science 256: 808–813).

Currently, a number of clinical studies are already being performed with this so-called ex vivo approach. This has lately involved the use of plasmid DNA, oligonucleotides, mRNA, genomic DNA, YACs (yeast artificial chromosomes), in addition to the retroviruses mentioned above, for the transfection of cell cultures. However, the ex vivo method involves a high expenditure of work and is not suited for the treatment of all diseases. There may be mentioned, for example, muscular dystrophy or cystic fibrosis. Thus, it is desirable to provide simpler procedures to administer therapeutically useful DNA to an organism. It has been found in this context that it is possible to administer plasmid DNA directly into the tissue of an organ. Part of the DNA will be transported to the nucleus. The genetic information administered via the DNA is translated there into the therapeutically active protein. The treatment within the organisms is a direct one and is called in vivo treatment.

For in vivo treatment, the DNA or RNA may also be mixed with liposomes or other substances, resulting in a better intake of the nucleic acids into the cell. However, the nucleic acid may also be directly injected into the organ to be treated, for example, a muscle or a tumor (Plautz, G. E. et al., 1993, PNAS, Vol. 90, 4645–4649). The advantage is that the DNA entering the organism does not cause any immunological reactions in the organism if it is free of accompanying immunogenic contaminations. Therefore, in vivo gene therapy makes high demands on the quality of the nucleic acids to be administered. The DNA must be free of toxic substances which might result in pathogenic effects in the organism to be treated. Clinical phase I studies on humans using this technology have resulted in rather detailed and strict requirements for the nucleic acids used therein. According to the requirements of the FDA in the U.S.A., the nucleic acids employed for therapeutical uses have to pass the following quality controls:

| Examination of the nucleic acid for: | requirement/limit |
| --- | --- |
| Endotoxins | <300 I.U./mg of DNA |
| E. coli genomic DNA | <50 µg/mg of DNA |
| Protein | <100 µg/mg of DNA |
| Supercoiled DNA | >90% |
| $A_{260/280}$ | 1.75–1.85 |
| Residual salt | scan from $A_{220}$ to $A_{320}$ |
| RNA | <1% |
| Sterility | no colonies after 14 days of tryptose culture |

In addition to the quality of the purified nucleic acid, the scale on which the nucleic acid can be purified is also of crucial importance. Thus, a future technology must enable to purify nucleic acids on a scale of from 1 mg to 100 kg which in turn requires culture volumes of from 1 l to 100 $m^3$.

A general problem in the purification of nucleic acids from bacterial cultures is at first the lysis of the microorganisms. In addition to the alkaline lysis described by Birnborn and Dohly (Nucl. Acids Res. 7, pages 1513–1522 (1979)) which is preferred herein, this may also involve the rupture of the bacterial cells by high pressure (French Press), lysis in the presence of detergents, or the application of heat (boiling lysis).

Subsequently, the nucleic acid can be separated more or less effectively from the other components of the bacterial cell, such as proteins or genomic DNA and metabolites, by various methods. The most simple, but also not very efficient, possibility is the separation by the addition of salts, such as LiCl, causing precipitation of the cellular proteins. The nucleic acid can subsequently be precipitated with alcohol. A drawback of this method is that contaminations of RNA, ssDNA and proteins cannot be separated off quantitatively. As an additional purification step, phenol extraction is frequently performed to remove any protein contaminations. The drawback of this method, desingated as "salting out", is that endotoxin contaminations as well as RNA and ssDNA which may be present cannot be removed. In addition, phenol extraction involves the risk of contaminating the nucleic acid with phenol. Further, phenol treatment of nucleic acids usually results in an increased content of so-called "nicked" nucleic acid, i.e. break of the nucleic acid strand at many sites, which in turn highly affects its stability.

CsCl gradient centrifugation has been an established method for the purification of nucleic acids for nearly 30 years. This makes use of the different sedimentation behaviors of differently sized nucleic acid molecules (RNA, plasmid DNA, genomic DNA) in a CsCl concentration gradient in the presence of intercalating agents, such as ethidium bromide, for the separation of nucleic acids. This type of separation can only be used with large quantities and requires the use of ultracentrifuges. In addition to the high financial expenditure of about DM 60,000.—per ultracentrifuge, another drawback is the considerable expenditure of time of at least 48 h for such a purification. This method achieves a yield of only 5 mg of nucleic acid at most per centrifugal run.

The purification of nucleic acids by chromatographic methods is also known per se. There are generally two types of distinct methods.

Purification by anion exchange chromatography is described in EP 0 268 946 B1. The bacterial cells are preferably lysed by alkaline lysis. The cellular proteins and genomic DNA are separated by means of detergents and subsequent centrifugation. The supernatant thus obtained which contains the plasmid DNA is called the "cleared lysate". The cleared lysate is further purified over an anion exchange column (QIAGEN®), wherein RNA and ssDNA are quantitatively separated off. Removal of endotoxins does not take place.

Gillespie and Vogelstein, Proc. Natl. Acad. Sci., USA, 76, p. 615–619, state that nucleic acids may be further purified by binding to silica gel or diatomaceous earth in the presence of chaotropic salts, such as GuHCl, NaCl etc. In contrast to anion exchange chromatography, binding of the DNA is here performed in the presence of high salt concentrations whereas elution is performed at low salt concentrations. The mechanism is not understood in all details, but it is considered that the nucleic acid is precipitated by dehydration on the surface of the silica gel particles. Since this involves binding and elution according to an "all-or-none" principle, a quantitative separation of RNA, ssDNA and proteins is not possible. Therefore, unfortunately, such DNA preparations are unsuited for obtaining nucleic acids for use in gene therapy due to RNA, protein and ssDNA contaminations. In addition, 1000 times higher endotoxin values can be found in such preparations.

The nucleic acids obtained should also be suited for use in gene therapy according to the "antisense" or "sense" strategy. "Anti-sense" strategy makes use of the tendency of, for example, mRNA to form hybrids with complementary nucleic acids. The hybrids are inactive. Thus, the "antisense" nucleic acid inactivates the mRNA. The "antisense" RNA obtained according to the invention may be administered to the subject to be treated continuously from outside or may be generated inside the subject himself by correspondingly transformed cells. The "sense" strategy involves a supplementation or assistance of, e.g., mRNA which serves important functions. The RNA required is administered to the subject to be treated. The nucleic acid to be obtained should also be suited for use in so-called genetic vaccination methods.

The quality requirements stated above cannot be satisfied by the DNA preparation methods described using cesium chloride gradient centrifugation or by the isolation of DNA in the presence of chaotropic salts alone since in this method the DNA to be isolated gets in contact with various toxic or cancerogenic substances, such as phenol, chloroform, guanidinium chloride, or ethidium bromide. Thus, it can be shown by electron microscopic analysis that ethidium bromide incorporated in the double helix cannot be completely removed any more (Schleef and Heinemann (Bio Techniques Vol. 14, No. 4, 1993). DNA molecules which are contaminated, e.g., with ethidium bromide in the course of the preparation may induce allergic reactions in the body due to the intercalated ethidium bromide so that any therapeutical approach with DNA thus prepared cannot be justified.

High purity DNA can be prepared with anion exchange chromatography without the use of toxic substances. However, even when chromatography is used, endotoxins can be conveyed into the nucleic acid and/or oligonucleotid fractions to a not unrisky extent.

The object of the invention is to provide a one-step process for the purification, isolation and preparation of nucleic acids which can meet the high quality requirements for nucleic acids and/or oligonucleotides for gene therapy. A drastic reduction of endotoxin levels should already take place, if possible, in sample preparation.

Surprisingly, the object of the invention is achieved by a process in which the anion exchange chromatographic material described herein is employed as follows.

In the manner described above, a cleared lysate can be obtained by various methods. In a preferred embodiment, the centrifugation step after the lysis for the separation of genomic DNA and SDS/protein complex can be dispensed with by using a filtration device as described in PCT/EP 95/00392. At the same time, such filtration enables a considerable reduction of the endotoxin contaminations of the nucleic acid solution.

By using the buffer proposed in WO 95/21179 in connection with anion exchange chromatography, gel filtration of binding to silica gel or diatomaceous earth in the presence of chaotropic salts in a one-step process, the nucleic acid can be purified to meet all quality requirements stated above.

The anion exchange material employed in the process according to the invention enables a neat separation of RNA and DNA due to the elution points differing by at least 100 mM NaCl.

The anion exchange material which can be used in the process according to the invention is also suited for the purification of virus particles, especially also intact virus particles, for in vivo/ex vivo gene therapy.

However, endotoxins may also be depleted or removed according to the method proposed in WO 95/21179. Endotoxins are depleted or removed therein by treatment with chromatographic material. After the lysis of the natural sources from which the nucleic acids and/or oligonucleotides are to be obtained, the fractions obtained are treated with metal-chelating chromatographic methods. This method may be employed in addition to or in combination with the incubation of the fractions obtained with aqueous salt solutions and detergents wherein the detergent treatment is followed by anion exchange chromatography. The metal-chelating chromatographic materials include chelating agents, IDA (iminodiacetate) or NTA (nitrilotriacetate), which are bound to supports, such as silica gel, diatomaceous earth, glass, aluminium oxides, titanium oxides, zirconium oxides, hydroxyapatite, dextrane, agarose, acrylic amide, polystyrene resins, or copolymers of the monomeric building blocks of the polymers mentioned. Other materials which may be used include polymyxin or DNA ETOX®. On this affinity support, nickel ions, for example, can be complexed which may interact with side-chain nitrogen containing amino acid residues in proteins through additional coordination sites. The lysed biological sources which have been freed from cell debris may be incubated, in particular, with Ni/NTA chromatographic material based on silica gel. The chromatographic material may be centrifuged off, for instance, after the incubation is completed, if batch-mode was used, and the supernatant may then be further processed according to the invention. In addition to batch mode, the affinity chromatography may also be performed in columns if the sample condition allows.

The nucleic acid to be isolated may be derived directly from cells which have been lysed. The process according to the invention ensures the separation of contaminants and yields nucleic acids having the purity required for gene therapy. Surprisingly, the commercial material QIAGEN® of the firm Qiagen, in particular, proves to be suitable for use in the process according to the invention.

This material enables a very efficient separation of the DNA from RNA. DNA elutes at a salt concentration corresponding to about 480 mM sodium chloride, whereas the double-stranded plasmid DNA elutes only at about 1260 mM sodium chloride. The difference between these two elution points is about 420 mM with the QIAGEN® material whereas the difference between the elution points of RNA and plasmid DNA is about 80 mM of sodium chloride concentration at most with all known anion exchange materials. Such a low difference in elution points involves a high risk of coelution of DNA and RNA, in particular with single-stranded DNA.

The material which is commercially available under the designation of QIAGEN® is particularly suitable for the purification of plasmid DNA for gene therapy. This chromatographic support material is a modified porous inorganic material. As inorganic support materials, there may be used materials such as silica gel, diatomaceous earth, glass, aluminium oxides, titanium oxides, zirconium oxides, hydroxyapatite, and as organic support materials, such as dextrane, agarose, acrylic amide, polystyrene resins, or copolymers of the monomeric building blocks of the polymers mentioned.

The anion exchanger which is preferably used may be obtained, for instance, by the reaction of one of the above-mentioned support materials in a first step with a silanizing reagent of the general formula I, $$R^1R^2R^3SiR^4 \qquad (I)$$

wherein $R^1$ is an alkoxy residue of from 1 to 10 carbon atoms, especially —OCH$_3$, —OC$_2$H$_5$ or —OC$_3$H$_7$, or a halogen atom, especially—Cl, or a dialkylamino group with identical or different alkyl residues of from 1 to 6 carbon atoms;

$R^2$ and $R^3$ are independently a hydrocarbon residue of from 1 to 10 carbon atoms, especially —CH$_3$, —C$_2$H$_5$ or —C$_3$H$_7$, or an alkoxy residue of from 1 to 10 carbon atoms, especially —OCH$_3$, —OC$_2$H$_5$ or—OC$_3$H$_7$, or a halogen atom, or an alkyl residue of from 4 to 20 carbon atoms which is interrupted by at least one oxa or amino group wherein said residue may also be substituted with one or more of halogen, cyano, nitro, amino, monoalkylamino, dialkylamino, hydroxy or aryl;

$R^4$ is a hydrocarbon chain of from 1 to 20 carbon atoms, or an alkyl residue which is interrupted by at least one oxa or amino group wherein said residue may also be substituted with one or more of halogen, cyano, nitro, amino, monoalkylamino, dialkylamino, alkoxy, hydroxy, aryl, and/or epoxy, especially

followed by a second step wherein the support which has been modified in the first step is reacted with a reagent of the general formula II:

$$X—R—Y \qquad (II)$$

wherein X is an amino, hydroxy, epoxy group or a halogen atom; R is a hydrocarbon chain of from 2 to 20 carbon atoms, or an alkyl residue which is interrupted by at least one oxa or amino group wherein said residue may also be substituted with one or more of halogen, cyano, nitro, amino, monoalkylamino, dialkylamino, alkoxy, hydroxy, aryl, and/or epoxy;

Y is a hydrocarbon residue having functional groups which form an anion exchange material and having from 1 to 10 carbon atoms which may be substituted with one or more of amino, monoalkylamino, dialkylamino, quarternary alkylamino.

In particular, support materials may be used made of silica gel and having diethylaminoethyl (DEAE) or diethylaminopropyl groups or dimethylaminoethyl (DMAE) or dimethylaminopropyl groups arranged on the surface thereof either directly or through so-called spacers.

In the process according to the invention, an anion exchanger is used, in particular, having the formula support material

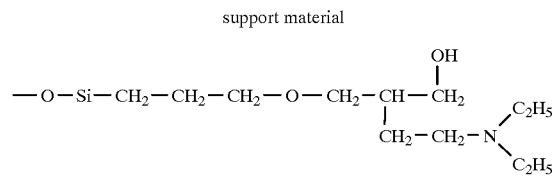

The ethyl groups of the amine may also be replaced by methyl groups.

The nucleic acids may also be purified by anion exchange materials based on polystyrene/DVB, such as Poros 20 for medium pressure chromatography, Poros® 50 HQ, of the firm of BioPerseptive, Cambridge, U.S.A., or over DEAE sepharose®, Q sepharose®, DEAE Sephadex® of the firm of Pharmacia, Sweden; DEAE Spherodex® LS, DEAE Spherosil®, of the firm of Biosepra, France.

Also, silica materials, such as kieselguhr, siloid®, diatomaceous earth, glass, silica gel, alumina, titania, hydroxyapatite, in the presence of chaotropic salts, such as sodium iodide, guanidinium chloride, and/or alcohols, are useful for the preparation of the nucleic acids according to the invention.

In the preparation of cell contents, especially nucleic acids, the problem frequently arises, to separate the lysed natural sources from which these contents are derived from the dissolved materials. The separation of the cells or cell debris is performed by centrifugation wherein the larger cell debris or cells will deposit as a pellet in the centrifuge tube. The cell contents are then found in the supernatant and may be pipetted. Filtration methods which are simpler per se could not prevail, in particular, in the preparation of nucleic acids since either the lysed cells or their fragments will pass through the too large-pored filters, resulting in turbidity and contaminations in the filtrate, or, when filters having appropriately small pores are used, obstruction of the filters will necessarily occur so that a reasonable preparation of the cell contents is no longer possible.

Usually, the samples are centrifuged in 50 to 500 ml vessels at about 20,000 rpm (about 30,000×g) for 5 to 60 min in order to remove cell debris.

Such centrifugation is time-consuming and with larger cell lysate volumes of 2 l and more can hardly be performed in an economical way. Although flow-through centrifuges exist, they are useful only for very large volumes of >1000 l. In addition, this is complicated and capital-intensive.

According to the invention, a simpler removal of cell debris from cell lysates of 1 l to 1000 l is enabled. This involves the use of the filtration methods described in WO 93/11218.

Also, an endotoxin depletion or removal is already performed in the separation of cell debris in an especially simple way according to the invention. This is done by using the method proposed in PCT/EP 95/00392. The lysate containing cell debris is passed over filter layers of glass, silica gel, diatomaceous earth, aluminium oxides, titanium oxides, zirconium oxides, hydroxyapatite, and other inorganic minerals, such as perlite®, or filter layers of interlaced non-wovens made of fiber glass and silica gel as well as cellulose, paper, pressed paper, interlaced or bonded non-wovens made of polymers, especially polypropylene, polyamides or polyester. Or it is passed over alumina or packed diatomaceous earth or interlaced or bonded non-wovens made of fiber glass and silica gel as well as cellulose, paper, pressed paper, non-wovens made of paper. The fraction emerging from the filter layer is collected and subsequently further treated according to the invention.

Surprisingly, it has been shown that endtoxins are depleted by such filtration. It is particularly preferred that the materials forming the filter layer bear hydroxy groups, or are coated or modified with organosilanes bearing or forming hydroxy groups, such as

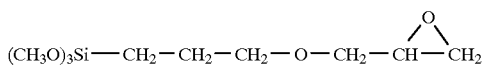

in particular, diol silica gel, diol diatomaceous earth and/or diol perlite.

In particular, packed diatomaceous earth has proven useful in the sample preparation for endotoxin depletion or removal.

The nucleic acid obtained by the process according to the invention is also suited for use in gene therapy according to the "antisensel" or "sense" strategy. "Antisense" strategy makes use of the tendency of, for example, mRNA to form hybrids with complementary nucleic acids. The hybrids are inactive. Thus, the "antisense" nucleic acid inactivates the mRNA. The "antisense" RNA obtained according to the invention may be administered to the subject to be treated continuously from outside or may be generated inside the subject himself by correspondingly transformed cells. The "sense" strategy involves a supplementation or assistance of, e.g., mRNA which serves important functions. The RNA required is administered to the subject to be treated. Due to its high purity, the nucleic acid obtained by the process according to the invention is also suited for use in so-called genetic vaccination methods.

In a preferred embodiment of the process according to the invention, the salts, which are necessary for eluting the nucleic acids under conditions of high ionic strength, are removed by treating with a mineral support material the fractions containing nucleic acids and having the high salt concentrations. These support materials essentially consist of non-modified inorganic support materials, e.g., glass or powdered glass. The nucleic acid will adsorb to such surfaces at high salt concentrations. Thereafter, the adsorbed nucleic acid can be desorbed with solutions of low ionic strength or demineralized water.

It has been found that the use of buffers containing isopropanol instead of those containing ethanol is advantageous. As proposed in WO 95/21177, particularly good transfection rates of the nucleic acids prepared according to the invention can be achieved by the use of buffers containing isopropanol.

According to the invention, a kit is also claimed containing components necessary for performing the process according to the invention. These include, in particular, reagents, also in concentrated form for final mixing by the user, chromatographic materials for the separation of the nucleic acids, aqueous solutions (buffers, optionally also in concentrated form for final adjusting by the user), and further auxiliaries, such as substances for the removal of endotoxins, such as diatomaceous earth, or chromatographic materials for desalting nucleic acids which have been eluted with sodium chloride.

The anion exchange material which may be used in the process according to the invention enables DNA preparations up to a kilogramm scale, especially in the range of from 10 mg to 100 g of DNA. An examination of the DNA which has been isolated by the process according to the invention by means of HPLC analysis and electron microscopy shows that such preparations are free of proteins (endotoxins), genomic DNA and RNA. The invention will be illustrated in more detail by the following examples.

Buffer P1: 100 μg/ml RNase A, 50 mM Tris/HCl,
(resuspension buffer) 10 mM EDTA, pH 8.0
Buffer P2: 200 mM NaOH, 1% SDS
(lysis buffer)
Buffer P3 3.0 M KAc, pH 5.5
(neutralisation buffer)
Buffer QBT: 750 mM NaCl, 50 mM MOPS, 15% alcohol*,
(equilibration buffer) pH 7.0, 0.15% Triton® X 100
Buffer QC: 1.0 M NaCl, 50 mM MOPS, 15% alcohol,
(wash buffer) pH 7.0
Buffer QN: 1.6 M NaCl, 50 mM MOPS, 15% alcohol,
(elution buffer) pH 8.5
TE: 10 mM Tris/HCl, 1 mM EDTA, pH 8.0
STE: 100 mM NaCl, 10 mM Tris/HCl, 1 mM EDTA, pH 8.0
Endotoxin Removal Buffer: 750 mM NaCl, 10% Triton® X 100, 50 mM MOPS, pH 7.0
As the alcohols, isopropanol or ethanol are preferably used.

EXAMPLE 1

Isolation of 50 mg of pSVCFTR from 10 l of *E. coli* culture for the aerosilation of CF patients The bacterial pellet resulting from 10 l of *E. coli* XL1 Blue fermenter culture is resuspended in 500 ml each of buffers P1 and P2. The mixture is incubated with 500 ml of buffer P3 on ice for 30 min and subsequently centrifuged at 20,000×g for 15 min. The supernatant is filtered over a folded filter for clearing. The filtered lysate is mixed with 1/10 of its volume of Endotoxin Removal Buffer (750 mM NaCl; 10% Triton® X 114; 40 mM MOPS, pH 7.0) and incubated on ice for 30 min. The lysate is now pumped onto a chromatographic column of 26 mm×100 mm filled with a QIAGEN anion exchanger (70–100 μm particle size, 2.5 μmol DEAE/g of chromatographic material) by means of a peristaltic pump and adsorbed. The chromatographic column is subsequently washed with 2000 ml of buffer QC at a flow rate of 15 ml/min. The plasmid DNA bound to the column is eluted with 280 ml of buffer QN at a flow rate of 3 ml/min. The eluate obtained is mixed with 200 ml of isopropanol and centrifuged at 20,000×g for 30 min. The resulting pellet is resuspended in 40 ml of TE buffer. The DNA thus purified is analyzed for purity by means of electron microscopy (EM), HPLC analysis, photometric measurement, agarose gel electrophoresis, and endotoxin test. This purification method results in a high purity DNA with no detectable contaminations of RNA, genomic DNA and endotoxins. The DNA thus isolated is mixed with a liposome solution and administered to CF patients by aerosilation in amounts of 10 μg.

EXAMPLE 2

Isolation of 10 mg of pCMVlacZ using QIAGEN tip 10,000 for the injection of plasmid DNA into striated muscle for the treatment of muscular dystrophy Five liters of a DH5alph/pCMVlacZ overnight culture are centrifuged, and the resulting pellet is resuspended in 125 ml of P1, mixed with 125 ml of buffer P2, and incubated at room temperature (RT) for 5 min. Then, 125 ml of buffer P3 is added, mixing is performed, followed by incubation at 4° C. for 30 min. The lysate is passed over a loose packing of diatomaceous earth in a filtration column as described in PCT/EP 95/00392 and subsequently spiked with 1/10 of its volume of Endotoxin Removal Buffer as in example 1 and incubated on ice for 30 min. The mixture is now spiked with 270 ml of isopropanol and centrifuged at 20,000×g for 30 min. The resulting pellet is dried ar RT for 10 min and resuspended in 5 ml of water. The resuspended DNA is spiked with 25 ml of QC buffer. This mixture is charged onto a DEAE silica gel column (26 mm ×50 mm, 70–100 $\mu$m, 2.0 $\mu$mol/g) equilibrated with 75 ml of QBT buffer. The column is then washed with 600 ml of QC buffer, and the DNA is then eluted with 75 ml of QF buffer. The eluate is mixed with 52.5 ml of isopropanol and centrifuged at 20,000 ×g for 30 min. The DNA pellet is dried at RT for 10 min and resuspended in 1 ml of PBS. The DNA solution can be used only for direct muscle injection.

EXAMPLE 3

Isolation of 100 mg of pXYHBV from a 20 l *E. coli* culture for use as "genetic hepatitis vaccine"

The bacterial pellet resulting from a 20 l fermentation run is resuspended in 1000 ml of buffer P1, spiked with 1000 of buffer P2 and incubated at RT for 5 min. After the addition of 1000 ml of buffer P3, the mixture is incubated at 4° C. for 30 min and subsequently centrifuged at 20,000×g. The supernatant is passed over a fiber glass filter, and the clear lysate is mixed with 2250 ml of isopropanol and centrifuged at 20,000×g for 30 min. The resulting pellet is resuspended in 10 ml of water and spiked with 90 ml of QC buffer. This mixture is pumped onto a chromatographic column according to example 1 by means of a peristaltic pump at a flow rate of 2 ml/min. The column is washed at a flow rate of 15 ml/min, and the DNA is subsequently eluted with 350 ml of QF buffer at a flow rate of 3 ml/min.

EXAMPLE 4

Removal of endotoxin from DNA preparations

The DNA prepared is adjusted to a final concentration of 0.1–1% with Triton® X 114. Then, the DNA/TRITON solution is incubated on a "roller" at 4–7° C. for 30 min. The solution is heated to room temperature and centrifuged at 20,000×g for 30 min or filtered. The supernatant is spiked with 0.7 volumes of isopropanol and precipitated. The resulting pellet is dried and resuspended in TE. The DNA thus treated is free of endotoxin.

EXAMPLE 5

Plasmid preparation

A 150 ml HB 101 *E. coli* culture with pUC 18 plasmid DNA in LB medium is centrifuged at 3000×g for 5 min to pelletize the cells. The cell pellet is resuspended in 20 ml of 50 ml Tris/HCl, 10 mM EDTA, pH 8.0, 100 $\mu$g/ml RNase A. Twenty milliliters of 0.2 M NaOH, 1% SDS are added to the cell suspension for cell lysis, cautiously mixed and kept standing at room temperature for 5 minutes. Then, 20 ml of 3 M potassium acetate, 2 M acetic acid is added for neutralisation, mixed, and incubated on ice for 15 minutes, and the cell lysate is sucked through the filter device according to the invention at a pressure difference of 2000 Pa to 80,000 Pa (20 mbar to 800 mbar). Alternatively, the sample may be pressed through the filter layers with a piston or by increased pressure. After the filtration, the filtration device is removed, and the filter cake with the cell fragments, denatured proteins and precipitated SDS is discarded. The filtrated lysate is mixed with 1/10 of its volume of Endotoxin Removal Buffer (750 mM NaCl; 10% Triton® X 114; 40 mM MOPS, pH 7.0) and incubated on ice for 30 min. The filtrate is completely sucked or pressed through the anion exchange column to achieve adsorption of the DNA. The extraction column is subsequently washed twice with 100 ml of 1 M NaCl, 15% ethanol, 50 mM MOPS, pH 7.0, to remove RNA and proteins. The DNA is eluted with 100 ml of 1.6 M NaCl, 15% ethanol, 50 mM MOPS, pH 7.0. The eluted DNA is precipitated with alcohol for desalting and concentrating, and the alcoholic pellet is pelletized by centrifugation.

Alternatively, the alcoholic precipitate of the nucleic acid may also be obtained by filtration. This has advantages when large amounts of DNA must be prepared and the volumes to be handled are larger than, for instance, 1 l.

EXAMPLE 6

A DNA template is transcribed into RNA via an in vitro reaction. The reaction solution is adjusted to 750 mM NaCl and purified over a QIAGEN® anion exchange column. The purified RNA is subsequently used for in vitro or in vivo gene therapy.

EXAMPLE 7

Purification of 40 mg of pBR322 using DEAE Q Sepharose® (firm of Pharmacia)

The biomass from a 40 l fermenter culture of pBR322 was lysed by alkaline lysis with 10 l each of buffers P1, P2, and P3. Subsequently, the lysate was passed over a filter device consisting of a loose packing and then incubated at 4° C. for 30 min. The DNA is now precipitated by the addition of 0.7 volumes of isopropanol 50 MM NaCl. The resuspended DNA solution is charged onto a DEAE Q Sepharose column with a bed volume of 200 ml. The DNA is eluted with a gradient of 1 mM NaCl/ml, the buffers having the following concentrations:
Buffer A: 10 mM Tris/HCl, 1 mM EDTA, 0.75 M NaCl, pH 8.0;
Buffer B: 10 mM Tris/HCl 1,mM EDTA, 0.85 M NaCl.

The flow rate is 0.5 ml/min. The DNA is subsequently precipitated with ethanol and resuspended in PBS buffer in a concentration of 1 $\mu$m/$\mu$l.

We claim:
1. A process for the isolation and purification of nucleic acids, oligonucleotides, or a combination thereof, from a bacterial or virus particle source, comprising the steps whereby:
   a) cells in said source are lysed to obtain fractions containing said nucleic acids, oligonucleotides, or combination thereof, and the fractions obtained are optionally freed from said source; followed by
   b) isolation of said nucleic acids, oligonucleotides, or combination thereof, by applying said fractions on an anion exchanger which begins desorbing DNA and RNA at different ionic strengths, such that DNA begins to desorb from the anion exchanger only at an ionic strength corresponding to a sodium chloride solution having a concentration higher by at least 100mM than the concentration of a sodium chloride solution corresponding to the ionic strength at which RNA begins to desorb form the anion exchanger material;
   c) eluting the nucleic acids, oligonucleotides or combination thereof, from the anion exchanger; and d) the nucleic acids, oligonucleotides, or combination thereof, are treated after either step a) or step c) with non-ionic detergents, affinity chromatographic supports or inorganic chromatographic material for the removal of endotoxins.

2. The process according to claim 1, wherein the anion exchanger comprises a porous support.

3. The process according to claim 2, wherein the inorganic support materials are selected from the group consisting of silica gel, diatomaceous earth, glass, aluminum oxides, titanium oxides, zirconium oxides, and hydroxyapatite, and the organic support material is selected from the group consisting of dextrane, agarose, acrylic amide, polystyrene resins, and copolymers, thereof.

4. The process according to claim 3, wherein said support is obtained by reacting one of the organic or inorganic support materials, in a first step, with a silanizing reagent of the formula I,

wherein $R^1$ is an alkoxy residue of from 1 to 10 carbon atoms, a halogen atom, or a dialkylamino group with identical or different alkyl residues of from 1 to 6 carbon atoms;

$R^2$ and $R^3$ are independently a hydrocarbon residue of from 1 to 10 carbon atoms, an alkoxy residue of from 1 to 10 carbon atoms, a halogen atom, or an alkyl residue of from 4 to 20 carbon atoms which is interrupted by at least one oxa or amino group and which is, optionaly, substituted with one or more of halogen, cyano, nitro, amino, monoalkylamino, dialkylamino, hydroxy or aryl;

$R^4$ is a hydrocarbon chain of from 1 to 20 carbon atoms, or an alkyl residue which is interrupted by at least one oxa or amino group and which is, optionally substituted with one or more of halogen, cyano, nitro, amino, monoalkylamino, dialkylamino, alkoxy, hydroxy, aryl, or epoxy, or combination, thereof

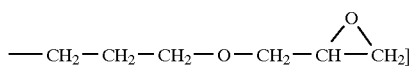

followed by a second step, wherein material resulting from the first step is reacted with a reagent of the formula II:

wherein X is an amino, hydroxy, or epoxy group or a halogen atom;

R is a hydrocarbon chain of from 2 to 20 carbon atoms or an alkyl residue which is interrupted by at least one oxa or amino group and which is, optionally, substituted with one or more of halogen, cyano, nitro, amino, monoalkylamino, dialkylamino, alkoxy, hydroxy, aryl, epoxy, or combination, thereof; and Y is a hydrocarbon residue having functional groups which form an anion exchange material and having from 1 to 10 carbon atoms, which is, optionally, substituted with one or more of amino, monoalkylamino, dialkylamino, or quarternary alkylamino.

5. The process according to claim 2, wherein diethylaminoethyl groups or dimethylaminoethyl groups are arranged on the surface of the support either directly or through spacers.

6. The process according to claim 1, wherein said nucleic acids, oligonucleotides, or combination, thereof, are selected from the group consisting of plasmid and cosmid DNA, DNA isolated from viruses, also DNA in enzymatically and chemically modified form, RNA, ribozymes, and combinations, thereof.

7. The process according to claim 1, wherein salts solutions are utilized for eluting the nucleic acids from the anion exchanger, which salts are removed by treating, with a mineral support material, eluate fractions containing said nucleic acids adsorb to the surface of said mineral support material, and subsequent desorption of the nucliec acids from the mineral support material is effected with water or buffer solutions of lower ionic strength than said salts solution.

8. The process according to claim 1, wherein cell debris of the cell lysate of step a) is separated off by filtration using a filter the pore size of which decreases in the direction of flow, a filter having a filter layer of glass, silica gel, alumina, packed diatomaceous earth, interlaced fiber glass, bonded non-woven fiber glass, silica gel, cellulose, paper, pressed paper, or non-woven paper.

9. The process according to claim 1, further comprising the step, whereby a preliminary purification of a sample of a cell lysate from step a) containing nucleic acids is performed on a layer of unmodified diatomaceous earth.

10. The process of claim 1 wherein the source is virus particles.

11. The process according to claim 1 wherein the eluting step is performed using a buffer solution containing isopropanol.

12. The process according to claim 1, wherein the anion exchanger includes a non-porous support.

13. The process according to claim 12, wherein the non-porous support is made of inorganic material.

14. The process according to claim 12, wherein the non-porous support is made of organic material.

15. The process according to claim 2, wherein the porous support is made of inorganic material.

16. The process according to claim 2, wherein the porous support in made of organic material.

17. A kit containing reagents, chromatographic materials for separation of nucleic acids, aqueous buffer solutions, and substances for the removal of endotoxins, which kit is useful for performing the process according to claim 1.

* * * * *

UNITED STATES PATENT AND TRADEMARK OFFICE
CERTIFICATE OF CORRECTION

PATENT NO.   : 5,990,301
DATED        : November 23, 1999
INVENTOR(S)  : Metin Colpan et al.

It is certified that error appears in the above-identified patent and that said Letters Patent is hereby corrected as shown below:

<u>Title page,</u>
Item [30], Foreign Application Priority Data, please add the following as follows:
-- Sep. 14, 1994 [DE] Germany ..................................... 44 32 654.8 --
-- Sep. 1, 1994 [DE] Germany .....................................44 31 125.7 --

Signed and Sealed this

Sixteenth Day of April, 2002

*Attest:*

JAMES E. ROGAN
*Attesting Officer*   *Director of the United States Patent and Trademark Office*